United States Patent [19]

Pravda

[11] Patent Number: 4,527,417

[45] Date of Patent: Jul. 9, 1985

[54] APPARATUS USEFUL FOR RAPIDLY DETERMINING THE MOLECULAR WEIGHT OF A FLOWING GASEOUS MATERIAL

[76] Inventor: Milton F. Pravda, 7708 Greenview Terr., Towson, Md. 21204

[21] Appl. No.: 589,020

[22] Filed: Mar. 13, 1984

[51] Int. Cl.³ .................................................. G01N 25/00
[52] U.S. Cl. .................................................. 73/23; 374/45
[58] Field of Search ...................... 73/23, 27 R, 26; 374/43, 44, 45, 54; 165/11 R, 30; 62/5

[56] References Cited

U.S. PATENT DOCUMENTS

| | | |
|---|---|---|
| 3,165,146 | 1/1965 | Smith et al. ............................ 73/23.1 |
| 3,173,273 | 3/1965 | Fulton ......................................... 62/5 |
| 4,067,203 | 1/1978 | Bohr ......................................... 62/208 |

*Primary Examiner*—Stephen A. Kreitman

[57] ABSTRACT

The molecular weight of a pressurized flowing gas is determined by means of a vortex tube. The temperatures of the inlet gas to the tube and of its outlet hot and cold gas fractions are sensed by e.m.f.-producing temperature sensing means; the resulting e.m.f.'s are fed to a divider circuit which amplifies them, forms differential e.m.f.'s and a ratio of the differential e.m.f.'s, and converts the ratio to the molecular weight of the gas.

3 Claims, 2 Drawing Figures

APPARATUS USEFUL FOR RAPIDLY DETERMINING THE MOLECULAR WEIGHT OF A FLOWING GASEOUS MATERIAL

CROSS-REFERENCE TO RELATED APPLICATION

This application contains matter disclosed in copending application Ser. No. 589,009 filed Mar. 13, 1984.

BACKGROUND OF THE INVENTION

1. Field of the Invention

The field of the invention comprises the determination of the molecular weight of a flowing gaseous material by means of a vortex tube.

2. Description of Prior Art

Heretofore, the molecular weight of a gas, as described in chemistry text books, has been determined in slow batch-type or single test procedures, one of which comprises measuring the volume of a weighed quantity of gas at an observed temperature and pressure, and using these data in the perfect-gas equation to calculate the molecular weight. Another comprises measuring the density, pressure, and temperature and calculating the molecular weight by aid of the perfect-gas equation rearranged to show the density. Still another is the Victor Meyer air displacement. No prior art flow methods capable of measuring the molecular weight of all gases or gas mixtures are known to applicant. Regarding the use of vortex tubes, applicant is aware of U.S. Pat. No. 3,165,146 which discloses a method for regulating the temperature of an instrument housing wherein the vortex tube is disposed within the housing, and temperature-controlled air is introduced to the tube. A thermocouple inside the housing and spaced some distance from the tube is used to sense the temperature in the housing and to influence the flow of temperature-controlled air thereto. The hot gas fraction of the vortex tube is removed from the housing while the cold gas fraction is discharged therein to cool the housing interior. This method is not concerned with molecular weight determinations.

SUMMARY OF THE INVENTION

The invention is directed to the use of a conventional vortex tube for determining the molecular weight of a flowing gas. As is known, a vortex is able to separate a gas fed to it into hot and cold fractions. The invention proposes to sense the temperatures of all three gas streams; i.e., inlet gas and the two fractions, by means of sensing means, preferably electromotive force (e.m.f.)—producing sensors, then by means of an electric circuit integrally arranged with and including said sensing means to obtain from such data differential e.m.f.'s that are proportional to the temperature differences existing between each fraction and the inlet gas, forming a ratio of the differentials, feeding the ratio to a meter, and reading the molecular weight on the meter. This ratio, it has been found, is characteristiic of the molecular weight of the inlet gas, may be duplicated in repeat tests, and can be used to find the molecular weight of the inlet gas.

The invention provides not only an easy, simple, and convenient means of determining the molecular weight of a gas but also a rapid one, requiring only an interval of less than a few seconds for a reading after the apparatus has been assembled and placed in working condition. Molecular weight readings can be taken continuously once the apparatus is made operational. The invention is useful where the test gas flow is from a batch supply or tank, or where the flow is from a continuous source, and in the latter case there is no interruption of the flow; in either case, the determination can be made without waste or destruction of the gas. The invention is of further value to enable gas phase chemical reactions to be followed by monitoring the molecular weight of the gaseous reactant mixture; a deviation from the proper molecular weight can be ascertained quickly and corrected. In a similar way, the dangerous or excessive presence of pollutants and/or toxic gases in a given environment can be made known. Other advantages will become apparent as the description proceeds.

BRIEF DESCRIPTION OF THE DRAWINGS

The invention is illustrated in the accompanying drawings, which are diagrammatic, and in which.

DESCRIPTION OF THE SPECIFIC EMBODIMENTS

Figure 1:
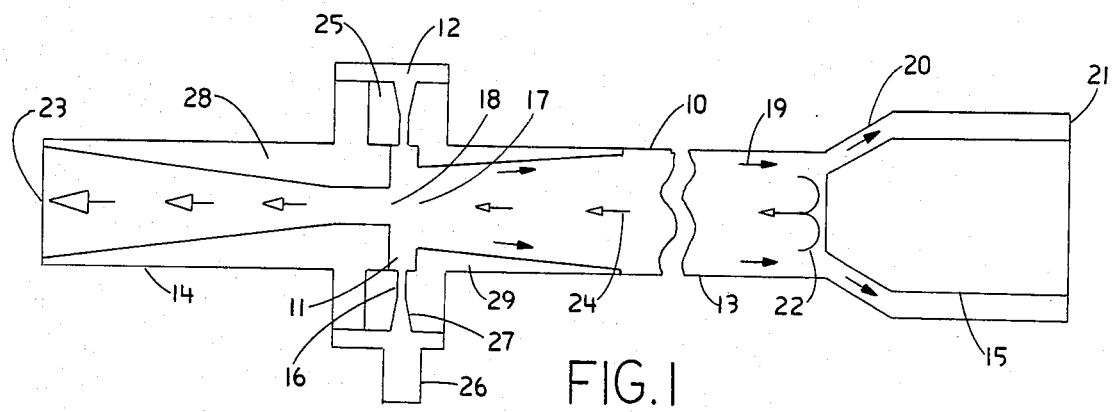
FIG. 1 is a schematic view of a conventional vortex tube showing internal arrangement.

Referring to FIG. 1, a conventional vortex tube 10 is seen as comprising a generation chamber 11, gas inlet chamber 12, a long open-ended tube 13, a short open-ended tube 14, a control valve 15, a generator 25, and a gas inlet tube 26. Nozzles 16, of which there are a plurality, introduce pressurized gas from inlet chamber 12 to chamber 11; these nozzles are to be understood as being more or less tangentially disposed relatively to chamber 11 so that they feed the gas thereto in a spinning or swirling stream or helical path; i.e., so that it has a rotational velocity. The vortex tube functions to cause the gas to flow into long tube 13, which is on one side of and in communication with chamber 11; and it will be noted that the opening 17 into such tube is larger than the opening 18 into the short tube. The spinning gas, located in a zone near the inside surface of tube 13, note 19, reaches the end 20 where it meets control valve 15 which allows part of the gas to escape; i.e., the spinning annularly located gas 19 flows out through hot end outlet 21. The remaining gas is forced to the center ot tube 13 where, still spinning, it reverses, note 22, and moves back toward the short tube 14, through the latter, and is removed through cold end outlet 23. Nozzles 16 are convergent; the converging portion being formed by cone surface 27. The maximum gas velocity through nozzles 16 into chamber 11 cannot exceed sonic velocity regardless of the magnitude of the pressure in inlet chamber 12. The short open-ended 14 is fitted with a diffuser 28 which reduces the cold gas velocity and further reduces the cold gas temperature at outlet 23. The generator 25 has a cylindrical extension 29 which forms a transition between opening 17 and the long open-ended tube 13.

Accompanying the separation of the inlet gas into two distinct spinning streams, one inside the other and moving in opposite directions in the long tube 13, is another observed phenomenon, namely, the temperature of the outer stream is increased while that of the inner stream is decreased. The temperature changes are considerable. These phenomena are referred to as the "heat-separation" effect in U.S. Pat. Nos. 2,907,174 and 2,955,432.

In sum, and after steady state operation is attained, it may be seen that the vortex tube produces a pair of rapidly rotating, coaxially disposed fractions, comprising a warmer outer annular fraction 19 and a colder inner core fraction 24. The temperatures of these fractions may be considered with reference to the temperature of the inlet gas; thus the temperature of the hot fraction is greater than that of the inlet gas, which in turn is greater than that of the cold fraction; symbolically, $T_h > T_i > T_c$. Conveniently, the warmer fraction is simply designated as "hot", and the colder fraction as "cold".

The foregoing briefly described construction, operation, and effects of a vortex tube are disclosed in greater detail in U.S. Pat. Nos. 3,173,273 and 3,208,229, which disclosures are incorporated by reference.

Figure 2:
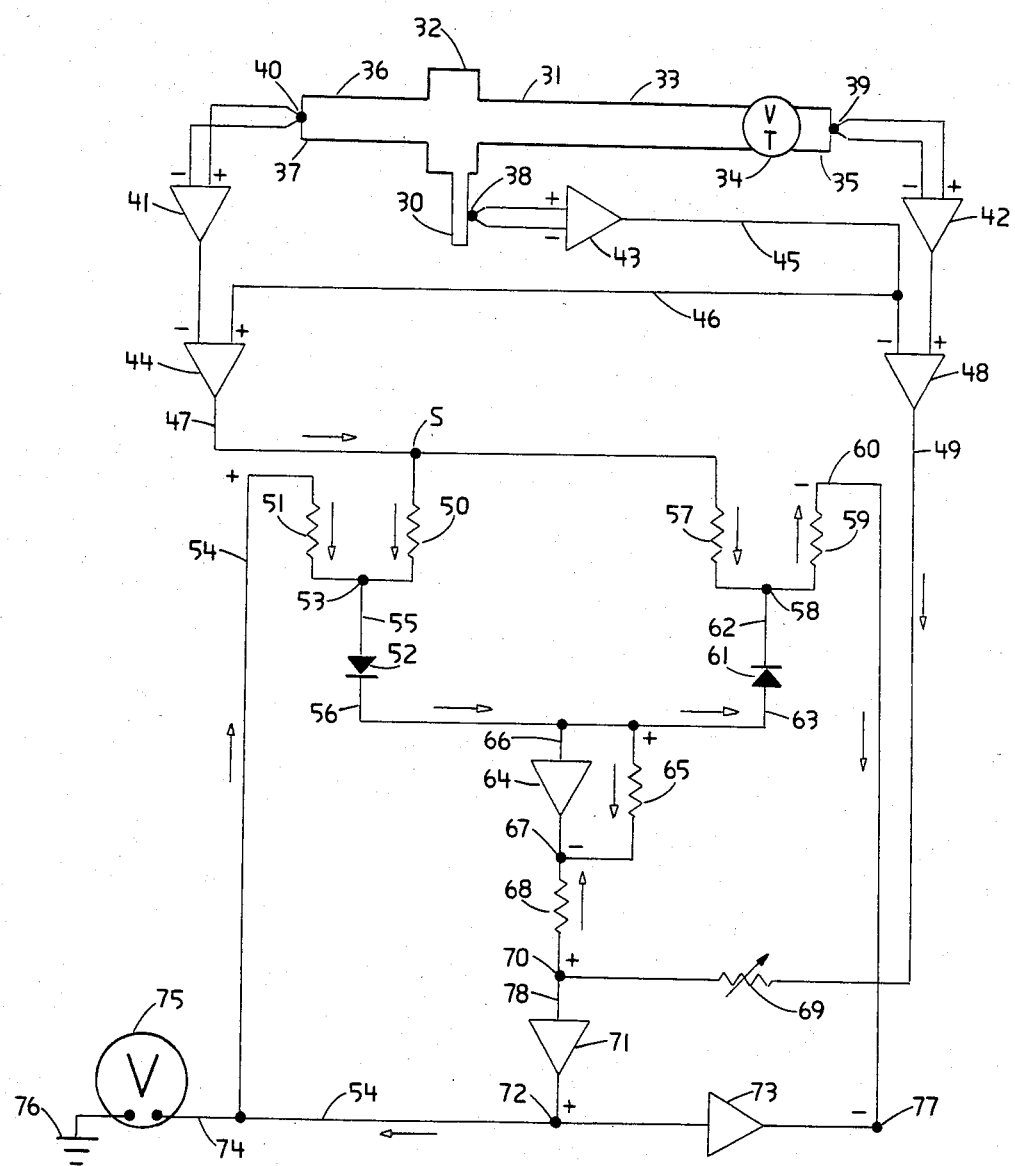
FIG. 2 is a combined gas flow and circuit diagram illustrating the introduction of test gas to the vortex tube and the temperature-sensing and signal-amplifying circuits associated therewith.

FIG. 2 illustrates the introduction of a gas to a vortex tube and the manner in which the temperatures of the inlet and the outlet gas streams may be sensed, the electronic circuit for handling the signals resulting from the sensing means, and the meter for reading the molecular weight. Briefly, pressurized test gas flows from a source not shown to inlet 30 of vortex tube 31. It passes to vortex generation chamber 32 where it is expanded, given the characteristic spinning or swirling motion, and separated by means of the heat-separation effect to form the above-described hot outer and cold inner fractions. The hot fraction passes out through long tube 33, valve 34, and hot outlet 35; the cold fraction leaves through short tube 36 and cold outlet 37. Temperature-sensing means are employed to sense the temperature of the gas streams, preferably means capable of generating an electromotive force, such as a thermocouple, which produces a small thermoelectricmotive force, on the order of millivolts, and even smaller, capable of accurate measurement. In FIG. 2, thermocouples 38, 39, and 40 sense the temperatures, respectively, of the inlet gas at inlet 30, the hot gas fraction at outlet 35, and the cold gas fraction at outlet 37, Thermocouple 38 may be secured to the outer wall of inlet 30, or may extend through the wall into the gas stream; thermocouples 39 and 40 are disposed in the gas streams. The e.m.f.'s produced by the thermocouples are, of course, related to the temperatures of the gaseous streams. The circuit produces from them differential e.m.f.'s that are proportional to the temperature differences existing between each gas fraction and the inlet gas, then a ratio of the differential e.m.f.'s, and then it converts the ratio to the molecular weight of the inlet gas under test. For convenience, these e.m.f.'s may be represented by the letter E, signifying voltage, and $E_c - E_r$, $E_h - E_r$, and $E_i - E_r$, respectively, represent the sensed e.m.f.'s of the cold, hot, and inlet gas streams, and where $E_r$ is the reference junction voltage. The voltage $E_r$ is the unavoidable reference junction voltage associated with all thermocouple circuits, and its value is established by the thermocouple type and by the temperature of amplifiers 41, 42, and 43.

More particularly, the temperature-sensed or sensor-derived e.m.f.'s are each uniformly amplified, forming amplified e.m.f. signals $E_c - E_r$, $E_i - E_r$, and $E_h - E_r$; these are passed to a pair of differential amplifiers, one of which produces a signal representative of $E_i - E_c$ and the other of which produces a signal representative of $E_h - E_i$; the outputs of the differential amplifiers are then fed to a divider circuit which forms a ratio of these signals; i.e., $k(E_h - E_i)/(E_i - E_c)$, where k is a ratio constant representing the ratio of the gain of differential amplifier 48 divided by the gain of differential amplifier 44; and this signal ratio is presented to a voltmeter having a scale calibrated in molecular weight units as well as or instead of voltage units.

In FIG. 2, the thermocouple e.m.f.'s are respectively fed to amplifier means 41, 42, and 43, each having a suitable and identical amplification factor or gain, for example 200, so that these e.m.f.'s are lifted in value in the millivolt range.

Low gain differential amplifier means 44 receives on its negative side the output from amplifier 41, and on its positive side the output from amplifier 43 through lines 45 and 46, and it produces a signal in line 47 which represents the difference between the two inputs and which maay be designated $E_i - E_c$. Similarly, low gain differential amplifying means 48 receives on its negative side the output from amplifier 43 through line 45, and on its positive side the output from amplifier 42, and it produces a signal in line 49 representing the difference between the two inputs, which may be designated $k(E_h - E_i)$.

To insure or satisfy circuit stability, the voltage output of differential amplifier 44 should at all times be greater than that of differential amplifier 48, and preferably it is about 2.5 times greater. For example, if means 44 has a gain factor of 10, then means 48 is selected to have a gain factor of 4; and if means 44 has a gain factor of 20, then means 48 has a gain factor of 8. The ratio constant k described previously will, therefore, have a preferred value of 4/10, or 8/20, or 0.4. When this ratio constant is multiplied by the sensor-derived differential signal ratio $(E_h - E_i)/(E_i - E_c)$, the product ratio will have a value less than unity regardless of the value of the molecular weight of the inlet gas being measured. In other words, the value of signal $k(E_h - E_i)$ is always less than the value of signal $E_i - E_c$. The signal $k(E_h - E_i)$ is the voltage in line 49 or $E_{49}$ and the signal $E_i - E_c$ is the voltage in line 47 or $E_{47}$.

At junction S in line 47 the signal is passed along two different paths, a first path starting with resistor 50 and a second path which begins with resistor 57, and in this sense S may be viewed as a junction means for sensing the flow along two different routes.

Means are now provided for establishing a current-voltage relationship in said first path according to which a change in voltage produces a changed current having a value proportional to the square of the average of the sum of the voltage signals through said path. Such current-voltage establishing means will become clearer in a moment, but first let it be noted that the means under discussion comprise the parallel resistors 50 and 51, both of equal value, and positively biased diode means 52. The flow of current from line 47 is down resistor 50 to junction 53, and the current flow down resistor 51 is from line 54, hereinafter described, to junction 53. At junction 53 the currents combine; the current in resistor 50 adds to that in resistor 51 at junction 53; and the voltage at that junction is the product of the combined current and the total parallel resistance of 50 and 51 and, further, can be shown to be the average of the sum of the voltage of line 47 and of line 54. In other words, at junction 53 the signal has an increased current value, and its voltage value has been added and averaged. Biased diode 52 will only allow current to pass from line 55 to line 56; it exhibits a characteristic current-voltage (I-E) relationship such that current passing through it is proportional to square of the voltage of line 55, ($I\alpha E^2$). Accordingly, owing to the action of the diode, the current in line 56 is proportional to the square of the average sum of the voltage of lines 47 and 54, and this relation may be written $$I_{56}\alpha((E_{47}+E_{54})/2)^2 \qquad (1)$$

Turning to the signal in line 47 from the point S to the second path, the current flow is down the resistor 57 and up the resistor 59; the current in 57 is the voltage of line 47 divided by the resistance of 57; the current in 59 is the voltage of line 60, hereinafter described, divided by the resistance of 59; and the current in 59 is also the sum of that in 57 and in line 62. Now, since the voltage of line 60 is at the back or exit end of resistor 59, and since the flow is conventionally regarded as passing from plus to minus, it follows that the voltage of line 60 has a minus value. At junction 58, the voltage value is equal to the total resistance of the parallel resistors 57, 59, multiplied by the current in line 62, and it can be shown that such voltage value is the average of the difference between the voltage of line 47 and that of line 60. The positive voltage signal of line 47 is subtracted from the negative signal of line 60, and the difference is averaged at junction 58. Biased diode means 61 permits current flow in only one direction, the up direction as shown, and it exhibits a characteristic current-voltage relationship such that current passing through it is proportional to the square of the voltage of line 62. Because of biased diode 61, the current in line 63 is proportional to the square of the average of the difference between the voltage of line 47 and that of line 60, and this relation may be written $$I_{63}\alpha((E_{47}-E_{60})/2)^2 \qquad (2)$$

The voltage of line 60 has a larger numerical value than that of FIG. 47; and, as this value is negative, a bias is imposed on the diode permitting the current to flow up.

The net effect is that current is subtracted from line 56 by virtue of the effect of diode 61. The combination of the two parallel equal-value resistors 57 and 59 with diode 61 constitutes a means for establishing a current-voltage relationship in the said second path according to which a change in voltage produces a changed current having a value proportional to the square of the average of the difference between the voltage signals through said path; and, as noted, such means function to subtract current from line 56.

Returning to line 56, the current there flows into line 63 and also to resistor 65; and, while some may flow into line 66, the amount is so small as to be negligible for the reason noted in the next paragraph. It follows that the current in line 56 is equal to the sum of that in line 63 and that in resistor 65; therefore, the current in line 56 is greater than that in line 63, and current will mainly flow from line 56 through resistor 65 in the direction indicated; i.e., from top to bottom. Since current flows from positive to negative, the polarities of resistor 65 are as indicated, and the voltage at junction 67 is negative. The current through resistor 65 may be written $$I_{65}=I_{56}-I_{63} \qquad (3)$$

Line 56 constitutes a transmitting means for passing along the output from the diode 52 having a current value diminished by the current in line 63 that flows to diode 61. This diminished output flows to a voltage-producing means comprising operational amplifier 64 and resistor 65. As is apparent, resistor 65 is in parallel with such means. Amplifier 64 has a high input resistance, typically one million ohms, and therefore, for all practical purposes, the current in line 66 will not enter it. Resistor 65 has a low resistance, and current will preferentially flow through it rather than in line 66, producing a voltage drop which is the product of the current and the resistance value of resistor 65. The net effect of operational amplifier 64 and parallel resistor 65 is to produce a voltage at junction 67. This voltage, as described, has a negative value; and by use of the foregoing equations (1), (2), and (3) this voltage can be shown to be proportional to the product of two voltages; i.e., that of line 47 and that of line 54, a fact that makes the voltage at junction 67 distinctive. The relation may be written $$E_{67}\alpha E_{47}\times E_{54} \qquad (4)$$

It follows, too, that the current through resistor 65 is also proportional to the product $E_{47}\times E_{54}$ because the value of resistor 65 is constant.

Resistors 68 and 69 are in parallel; and, although 69 is variable, for the moment let it be assumed that both have the same value. In resistor 68 the flow is up because at junction 67 the polarity is negative and current flows from plus to minus. The purpose of resistors 68 and 69 is to form an average voltage signal at junction 70 which is the difference between that of line 49 or $E_{49}$ and that at junction 67 or $E_{67}$, and using equation (4) it can be shown that $$E_{70}\times \tfrac{1}{2}(E_{49}-c(E_{47}\times E_{54})) \qquad (5)$$

where c is a constant inserted to eliminate the proportionality symbol in equation (4). In line 78 the current is equal to that in resistor 69 (or in line 49) minus that in resistor 68. Thus resistors 68 and 69 function as a means to form the average voltage signal described by equation (5), and it has a positive polarity.

The voltage at junction 70 is amplified in high gain amplifier 71, and the signal is delivered to junction 72 which is also the voltage of line 54. From junction 72 the positive signal is also applied to unity gain inverting amplifier 73 which delivers a negative signal of the same numerical value as that at junction 72 to point 77, and this applies the described negative bias on diode 61 through line 60. The signal in line 54 applies a positive bias on diode 52 and also is delivered to voltmeter 75 having in its casing the ground 76. The meter has dial means (not shown) in the form of a calibrated scale reflecting a voltage-molecular weight relationship and able to indicate the molecular weight of the flowing inlet gas stream.

The foregoing description may be enlarged upon in several matters, starting with the differential amplifiers represented as 44 and 48. The purpose in 44 is to have the amplified voltage $E_i-E_r$ buck the amplified $E_c-E_r$ input so that a difference $E_i-E_c$ is formed and delivered as amplified output in line 47; and in 48 the amplified input $E_h-E_r$ bucks amplified $E_i-E_r$ so that the difference $E_h-E_i$ is amplified and delivered to line 49. In the process of forming the differences, the reference junction voltage $E_r$ is obviously eliminated; that is, the temperature at which the apparatus operates will not affect its calibration.

As equation (4) indicates, the voltage formed at junction 67 is the result of a multiplying action carried out by the resistors 50, 51 and diode 52, and by the resistors 57, 59 and diode 61, all of which may be regarded as a multiplying circuit, sometimes referred to as an analog multiplier when coupled to operational amplifier 64 and parallel resistor 65. The voltage at 67 is proportional to the product of the voltages of lines 47 and 54, and this is of significance as described below. Before leaving the multiplier circuit, it may be noted that resistors 50, 51 and diode 52 comprise one-half of this circuit, and resistors 57, 59 and diode 61 the other half, that resistors 50, 51, 57, and 59 have equal resistance values, that diodes 52 and 61 have matched current/voltage characteristics, and that the signal in line 47 can be described as being fed to each half. At junction 53, resistors 50 and 51 form an average voltage signal from the sum of the signals in lines 47 and 54; and, at junction 58, resistors 57 and 59 form an average voltage signal from the difference between the signals in lines 47 and 60.

With regard to the constant c inserted in equation (5), it has been stated previously that the voltage signal presented to the voltmeter is $k(E_h - E_i)/(E_i - E_c)$, and that the voltmeter has a scale calibrated in molecular weight units as well as or instead of voltage units. The construction of a voltmeter is more sturdy than the construction of a millivoltmeter and, therefore, it is desirable to lift the signal presented to the voltmeter out of the millivolt range. In the illustrated example to follow, the voltmeter reads 4.0 volts when the ratio $E_h - E_i/E_i - E_c$ is equal to 1. When this ratio is multiplied by the 0.4 preferred value of the constant k, the voltmeter would normally read 0.4 volt instead of the desired 4.0 volts. As will be made clear in the illustrated example, the value of the constant c required to give a voltmeter reading of 4.0 volts is 0.1.

Regarding the product, $c(E_{47} \times E_{54})$, of the multiplying action, this is equal to the voltage of line 49 or $E_{49}$. This may be explained in the following way, starting with equation (5) above which gives the voltage at junction 70. In amplifier 71 this voltage is multiplied by a gain, designated A, so that at junction 72 the voltage is defined thus $$E_{72} = A/2(E_{49} - c(E_{47} \times E_{54})) \tag{6}$$

which may be written $$2E_{72}/A = (E_{49} - c(E_{47} \times E_{54})) \tag{7}$$

and if A is large, for example 100,000, the left hand side of equation (7) can be neglected; i.e., assigned a value of 0. Then $E_{49} - c(E_{47} \times E_{54}) = 0$ and $E_{49} = c(E_{47} \times E_{54})$ and $E_{54} = E_{49}/cE_{47}$. Thus, it may be said that the voltage of line 54 is equal to that of line 49 divided by that of line 47 multiplied by the constant c; and this illustrates the divider action of the circuit in FIG. 2. The point at which the dividing takes place is junction 72. Without the product, $E_{47} \times E_{54}$, one does not get the dividing action. The voltmeter measures the signal in line 54, which is equal to $E_{49}/cE_{47}$; and, as is clear from FIG. 2, this ratio is proportional to the ratio described earlier, $k(E_h - E_i)/E_i - E_c$. The constants c and k, as is well known, do not affect the proportionality of these two ratios.

Variable resistor 69 is operative to vary the voltage at junction 70, for by changing this resistance one also changes the voltage. In the factory, resistor 69 would be set equal to resistor 68, and valve 34 would be adjusted (with air as the test gas) so that the voltmeter read the molecular weight of air; in field use, if the apparatus lost calibration, trim resistor 69 would be adjusted so that the meter read the correct molecular weight for air.

The circuit comprising resistors 51, 50, 57, and 59, diodes 52 and 61, operational amplifier 64 and parallel resistor 65, resistors 68 and 69, high gain amplifier 71 and unity gain inverting amplifier 73 is sometimes referred to as an analog divider circuit. The inputs to this circuit are lines 47 and 49 and the output is line 74.

ILLUSTRATED EXAMPLE

An illustration may be given of the apparatus of FIG. 2, using as a basis a set of assumed but conventionally-encountered temperatures of the three gas streams: 32° F. for the cold gas fraction, 67° F. for the inlet gas, and 102° F. for the hot gas fraction. Let it also be assumed that the thermocouple sensors are iron-constantan and, as a matter of convenience, that the reference junction temperature $E_r$ is 32° F. so that Table 18 on page 73 of NBS Circular 561 may be used directly to obtain the sensor e.m.f.'s. The e.m.f.'s corresponding to these temperatures are 0 millivolt (0.0 volt), 1.0 millivolt (0.001 volt), and 2.0 millivolts (0.002 volt). Using the symbols noted above, $E_c$ is 0.0 volt as may have been produced by thermocouple 40, $E_i$ is 0.001 volt as may have been produced by thermocouple 38, and $E_h$ is 0.002 volt as may have been produced by thermocouple 39.

If amplifiers 41, 43, and 42 each have an output gain of 200, then the voltages of each output are 0.0, 0.2, and 0.4 volt, respectively.

Taking a gain of differential amplifiers 44 and 49 to be 10 and 4, respectively, the output of line 47 is (0.2−0.0) times 10 or 2.0 volts, and that of line 49 is (0.4−0.2) times 4 or 0.8 volt.

Coming to the diodes, as is described below, the input to diode 52 from line 54 is 4 volts, and to diode 61 from line 60 it is −4 volts. At junction 53 the voltage is the average of lines 47 and 54, or ½(2+4) or 3 volts; and at junction 58 it is the average of lines 47 and 60, or ½(2−4) or −1 volt. In line 56 the current is proportional to $E^2$ or $3^2$ or 9, and this is divided by 100 to compensate for typical diode characteristics, so that the value is 0.09 ampere. In line 63 the current is proportional to $E^2$ or $(-1)^2$ or +1, which is divided by 100, since diodes 52 and 61 have matched characteristics, to give 0.01 ampere.

The current in resistor 65 is that in line 56 minus that in line 63 or 0.09−0.01 or 0.08 ampere (designated $I_{65}$).

At junction 67 the voltage is $I_{65} \times R_{65}$. The resistance of resistor 65 and the gain of amplifier 71 are selected to produce a voltage of 4 volts at junction 72. The voltage at junction 72 would be the same as in line 54, or 4 volts; and at point 77 it is the same as in line 60, or −4 volts. The voltage signal to the voltmeter 75 transmitted by line 74 is also 4 volts.

At junction 72, the following equalities exist $$E_{72} = E_{54} = E_{49}/cE_{47} = k(E_h - E_i)/c(E_i - E_c) = k(T_h - T_i)/c(T_i - T_c) \tag{8}$$

because, as previously described, $E_{49} = k(E_h - E_i)$ and $E_{47} = E_i - E_c$; where, in this case, $E_h$, $E_i$, and $E_c$ have each been amplified. The preferred value of the constant k is 0.4. For a voltage at junction 72 of 4 volts, the value of the constant c is almost exactly 0.1. Substituting the initial values of $E_h$, $E_i$, $E_c$, $T_h$, $T_i$, $T_c$, used in this illustration, the derived values for $E_{49}$ and $E_{47}$, and the above values of the constants c and k in equation (8), the following is obtained $$4.0 = 4.0 = 4.0 = 4.0 = 4.0 \quad (9)$$

This illustration demonstrates that the apparatus of FIG. 2 will indicate the molecular weight of the inlet gas which is in accord with the disclosure in copending application Ser. No. 589,009.

It will be observed, on further examination of NBS Circular 561, that the thermocouple produced e.m.f.'s versus the temperatures sensed relationship is not precisely linear. This results, for iron-constantan thermocouples, in a differential voltage ratio which is a few percent higher than the corresponding differential temperature ratio. This nonlinearity is a common problem with temperature sensors, including all thermocouple types. The calibrated scale of this apparatus, reflecting the voltage-molecular weight relationship, will be suitably offset to correctly indicate the molecular weight of the flowing inlet gas stream.

This concludes the illustrated example.

For convenience of description in the claims, the foregoing references to resistors and junctions, which occur repeatedly, may be identified in an orderly manner as follows: resistors 50, 51, 57, 59, 65, 68, and 69 may be viewed as a first, second, third, fourth, fifth, sixth, and seventh resistor, respectively, and junctions 53, 58, 67, 70, and 72 may be viewed as a first, second, third, fourth, and fifth junction. These junctions are also describable as means for applying or sending the signal along different paths. Lines like 47, 49, 54, 56, 60, 63, 66, 74, and 78 may may be seen as comprising connecting means for transmitting signals.

Turning now to the inlet gas, its pressure is suitably in the range of 50 to 60 psig (3.515 to 4.640 kg/cm$^2$), and preferably 54 to 66 psig (3.796 to 4.640 kg/cm$^2$) when the hot and cold gas fraction exit pressures are ambient (0 psig) and when thermocouples are placed in their exits. It is understood that, if the hot and cold fraction exit pressures are elevated above 0 psig, the inlet gas pressure range must also be elevated by the same amount. It will be appreciated that these pressures are below those which impact sonic velocity to the spinning gas in the vortex tube. It has been noted that, where the inlet gas is a mixture of two single gases, pressures above the described ranges tend to cause the mixture to begin to separate into its constituent gases and to also cause a choking effect to occur in the converging tangential nozzles. Pressures below the described ranges tend to reduce the temperature differences and to result in inaccuracies in measurements.

Filtration by means of a suitable filter is useful to remove any moisture. The filter may simply comprise a fine mesh screen, but may also include one or more chemical dryers. The aim is to exclude all moisture and dirt from the gas entering the vortex tube. The condition of the test gas must be taken into account to provide pretreatments that will meet this aim. Thus, some gases may require use of a coarse filter to remove larger particles of dirt, soot, rust flakes, oil, etc., that may be present; and/or means such as a valve may be present to drain water from the filter bowl where the initial gas is saturated with moisture, followed by a condenser to cool the gas and a trap to remove condensed water; and/or a further treatment may comprise passing the de-watered gas to a fine filter to remove fine particles.

The thermocouples, it used as the sensing means, may be chosen from those generally available, of which a number are disclosed in the Handbook of Chemistry & Physics on pages E-106 to E-114 in the 56th edition or in the National Bureau of Standards, Reference Tables for Thermocouples, NBS Circular 561. Desirably, the combination of metals chosen should be one yielding the largest absolute e.m.f. for a given temperature, such as chromel-alumel, iron-constantan, copper-constantan, etc.

The throttle valve (note 34 in FIG. 2) of the vortex tube is set to produce a flow reversal of the inlet gas in the vortex tube. This valve controls the amount of hot gas exiting from outlet 35, and also the amount of cold gas leaving outlet 37. The particular setting can be described in said copending applicatiion Ser. No. 589,009 wherein the $T_h - T_i/T_i - T_c$ ratio was equal to one, using air as the test gas. At such ratio the long tube 33 will be found to be decidedly warm to the touch and the short tube 36 decidedly cool, and it is convenient to check the operation of the vortex tube by touching these outlet tubes. At such setting it can be shown that substantially equal amounts of air exit from the hot and cold ends of the tube. For field use, air is a convenient gas to obtain the desired setting since it is available generally in compressed form. It will be understood that other settings could be employed, and test gases other than air could be employed to obtain them.

During use, the vortex tube is well insulated, as with fiber glass or other suitable material, to avoid heat losses. The hot and cold fractions emerging from the tube may be discarded if their amounts are small; such losses can be kept small by using a tube of small size. The fractions may also be recovered and recycled to the inlet gas supply, care being taken to reintroduce them without disturbing the pressure of the gas to be tested, or the exhaust pressures of the hot and cold fractions.

Any suitable gas may be tested, including the so-called inert gases of Group 0 of the Periodic Table; the normally gaseous elements of Group 7a; common gases like hydrogen, nitrogen, oxygen, and air; the various normally gaseous oxides of nitrogen and sulfur; normally gaseous hydrocarbons and chlorinated hydrocarbons; commercially important synthesized gases like ammonia and the normally gaseous "Freons" comprising fluorocarbons; also normally gaseous fluorinated and chloro-fluorinated compounds, etc. Also gases like carbon monoxide, cyanogen, hydrogen chloride, hydrogen bromide, hydrogen iodide, hydrogen sulfide, methyl amine, methyl ether, etc. Single gases or a mixture of single gases are suitable. The invention is of particular value to test a gas suspected or thought to be impure as the determined molecular weight would throw light on the question. As another example: if a piece of equipment is charged with a "Freon" type gas and records are unavailable to establish its identity, the invention can be of service by revealing its molecular weight as a step towards identifying it. In general, the gas to be tested will be known, and it may be mixed with one or more other gases. Before testing, it should of course be free of moisture and dirt. In this connection the expression "gas" or "gaseous material" is, as a matter of convenience, intended to denote a single gas, pure or impure, or a mixture of two or more single gases, or a vapor or mixture of vapors.

Of pertinent interest is the application of the invention to determine the molecular weight of a gaseous reactant mixture which is used in a gaseous phase reaction to produce one or more products and wherein the reaction is incomplete, leaving an amount of unreacted reactants which it is desired to reuse. Initially, the proper proportions of the reactant mixture are known accurately; but, after the unreacted components are recycled and mixed with fresh reactants, the resulting mixture is changed such that the reactant proportions may no longer be proper for the reaction. A rapid determination of the molecular weight of the last-named mixture by means of the invention will be of value since it will signal whether or not it is necessary to add more of one reactant or another before sending the mixture to the reactor.

One such gas phase reaction is the high temperature-high pressure synthesis of ammonia from nitrogen and hydrogen $$N_2 + 3H_2 \rightarrow 2NH_3, \qquad (10)$$

by affording an easy and convenient way to control accurately the proportions of nitrogen and hydrogen. This reaction is carried out at 400° to 600° C., a pressure of 100 to 1000 atmospheres, and in the presence of a heterogeneous catalyst like iron plus iron oxide. As the equation shows, the reactant mixture consists of 1 mol or volume of nitrogen and 3 mols or volumes of hydrogen, or 25% nitrogen and 75% hydrogen, and has a molecular weight of $(28 \times 25\%)$ plus $(2 \times 75\%)$ or 8.5 at standard conditions. If the mixture has a molecular weight above 8.5, excess nitrogen is considered to be present; while below 8.5 there is excess hydrogen. Excess reactant will not enter into the reaction; and, therefore, the energy required to bring it up to reaction temperature and pressure is wasted. The invention can be of benefit to this reaction in two ways. First, it can insure the correct proportion of nitrogen and hydrogen in the original reactant mixture, and this may be done by passing the mixture to the inlet of the vortex tube and determining the molecular weight in the manner described; if it varies from the desired value of 8.5, the mixture is passed to an adjustment zone for addition of nitrogen or hydrogen, after which it is pressurized and sent to the reactor. Of course, if no adjustment is required, it is passed unaltered through the adjustment zone, or the latter is bypassed, and it is pressurized and reacted. Such determination of the molecular weight, and the adjustment of the proportions, may be performed in a continuous manner as well as batchwise.

The second way in which the invention can benefit the reaction involves the recycling of the unreacted gases. As the conversion is usually of the order of up to 25%, substantial quantities of unreacted gases are involved and, furthermore, if the amount of recycled nitrogen or hydrogen is excessive, the proportion of that gas in the reactant mixture (original mix plus recycled material) can build up rapidly and reduce the production rate. According to the invention, it is proposed that after the reaction mixture leaves the reaction zone, and after conventional separation of the ammonia product as liquid ammonia, the unreacted gases be combined with fresh charge, the pressure adjusted, the molecular weight of the resulting mixture be determined as described above, the reactant proportions be adjusted if necessary, and the process continued in an uninterrupted way.

The preceding description of ammonia synthesis is applicable to the Linde process, which employs substantially pure hydrogen from the electrolysis of water and substantially pure nitrogen from the liquefaction of air. It is also of interest in connection with the Haber process, which employs hydrogen obtained from water gas and nitrogen from producer gas.

Another reaction in which the invention may be applied is that of the U.S. contact process for making sulfur trioxide by the oxidation of sulfur dioxide, an important step in the manufacture of sulfuric acid, $$2SO_2 + O_2 \rightarrow 2SO_3 \qquad (11)$$

The reaction is carried out at a preferred temperature of 425°–250° C. and a pressure in the range of 5 to 30 atmospheres. According to this equation, the reactants comprise 2 mols or volumes of sulfur dioxide and 1 mol or volume of oxygen, or 66.6% dioxide and 33.3% oxygen; but in this process, using a catalyst like platinum on a support of vanadium pentoxide, the amount of oxygen is generally in excess, usually twice the stoichometric amount, so that the reactants comprise 2 mols of each gas, or 50% dioxide and 50% oxygen. The original reactant mixture has a molecular weight of $(64 \times 50\%)$ plus $(32 \times 50\%)$ or 48. Using the method of the invention to monitor the reactant mixture, the molecular weight to be determined by the vortex tube is to be compared with this value; and a value greater than 48 signifies excess dioxide and requires addition of oxygen to the mixture, while one less than 48 signifies excess oxygen and requires more dioxide. Following adjustment of concentrations, if necessary, the mixture is pressurized and sent to the reactor.

A further reaction for employment of the invention is the burning of hydrogen in an atmosphere of chlorine to form hydrogen chloride, $$H_2 + Cl_2 \rightarrow 2HCl, \qquad (12)$$

which may be carried out in a nonexplosive way at room temperature in the absence of bright sunlight. As is apparent, the reactants consist of 1 mol or volume of hydrogen and 1 mole or volume of chlorine; the molecular weight is $(2 \times 50\%)$ plus $(70.9 \times 50\%)$ or 36.5. A reactant mixture having a greater molecular weight than 36.5 has excess chlorine and requires addition of hydrogen, while one with a lower value has excess hydrogen and requires addition of chlorine.

The presence of toxic gases in an industrial or other working atmosphere may be detected and monitored. One first obtains a molecular weight value of the gases in the atmosphere in a toxic gas-free state for use as a standard of comparison; and then the working atmosphere is monitored by the present method, either on an intermittent or continuous basis, so that a determined molecular weight value differing from the standard is sufficient to alert observers to investigate and to take suitable action. This application of the invention is of interest where the atmospheric environment in question is known to be susceptible to the leakage or presence or formation of toxic gases, especially those that are odorless, like carbon monoxide, but also including other gases, particularly in small "hard-to-notice" amounts, such as the "Freons", chlorinated hydrocarbons, ammonia, acetone vapors, sulfur dioxide, methane, other normally gaseous hydrocarbons and normally liquid hydrocarbons having an appreciable vapor pressure. It is considered that the invention will be useful to monitor such atmospheres when they contain substantial proportions of toxic or pollutant gas or gases, say at least 1%, and preferably 2% or more.

Related to the foregoing application is the use of the invention to monitor the presence of high concentrations of unburned hydrocarbons in automobile exhaust gas. The latter is rather a complex mixture comprising gases brought in with the oxidizing air (nitrogen, oxygen, carbon dioxide, argon, etc.) and gases resulting from the combustion of the hydrocarbon fuel, including unused oxygen, carbon dioxide, carbon monoxide, water vapor, oxides of nitrogen, and unburned hydrocarbons. Before the mixture can be tested, it must be freed of all moisture and all dirt, both coarse and fine. Then its molecular weight may be determined as above described. A molecular weight for use as a standard must be obtained using a moisture-free dirt-free hydrocarbon-free exhaust gas, and the two values compared. It is contemplated that the presence of higher concentrations of unburned hydrocarbons, say 5000 p.p.m. and up, may be detected. Exhaust gases resulting from other fuels and from any internal combustion engine may be so monitored.

In connection with test gases that are, or may contain, toxic materials and/or pollutants which may be corrosive to the vortex tube material, it is advisable to use a tube, or parts thereof, made of a chemically inert material, such as a plastic or ceramic. Useful plastics include Teflon, which is a fluorocarbon resin, and methyl methacrylate. Regardless of the material, the tube may have a varying capacity, ranging from less than 1 to 100 or more cubic feet per minute (0.42 to 47.19 liters/sec).

It will be understood that the invention is capable of obvious variations without departing from its scope.

For example, the d'Arsonval/Weston voltmeter 75 can be replaced by a suitably calibrated digital voltmeter. The temperature sensing means may include resistance temperature detectors (RTD) with suitable circuit modifications to produce e.m.f.'s. Bead type thermistors may also be employed as the temperature sensing means. Care must be exercised to keep the temperature sensor size small in comparison with the sizes of the hot and cold fraction exits; otherwise, excessive backpressures will be experienced and the apparatus will not function as intended. This last consideration is especially important in miniaturized versions of the apparatus. Another obvious variation is to provide two inlet gas temperature sensing means, and connecting the hot fraction temperature sensing means to the first inlet gas temperature sensing means in a bucking mode directly forming a difference signal, and connecting the cold fraction temperature sensing means to the second inlet gas temperature sensing means in a bucking mode directly forming a difference signal. In this latter variation, the differential amplifiers may be eliminated.

In the light of the foregoing description, the following is claimed.

I claim:

1. Apparatus for determining the molecular weight of a flowing gas stream comprising in combination
 a vortex tube having an inlet for said stream, a vortex generation chamber for receiving the stream and separating it into a cold fraction and a hot fraction, and an outlet for each said fraction through which it exits from the tube as a stream,
 temperature-sensing means disposable in each stream for sensing the temperature thereof and coincidentally therewith producing an e.m.f. related thereto,
 said e.m.f.'s being designated $E_c$, $E_i$, and $E_h$, and being respectively produced in said cold, inlet, and hot streams,
 differential means for receiving each of said e.m.f.'s; the first of said means receiving the $E_c$ and $E_i$ signals and the second said means receiving the $E_h$ and $E_i$ signals,
 said first differential means producing an output signal, designated $E_i - E_c$, representing the difference between said two inputs thereto,
 said second differential means producing an output signal, designated $E_h - E_i$, representing the difference between said two inputs thereto,
 analog divider means for receiving output signals from said first and second differential means and forming a positive quotient signal therewith,
 and connecting means for transmitting said positive quotient signal from said analog divider means to a voltage sensing means having means relating said positive quotient signal to the molecular weight of said inlet gas.

2. Apparatus for determining the molecular weight of a flowing gas stream comprising in combination
 a vortex tube having an inlet for said stream, a vortex generation chamber for receiving the stream and separating it into a cold fraction and a hot fraction, and an outlet for each said fraction through which it exits from the tube as a stream,
 temperature-sensing means disposable in each stream for sensing the temperature thereof and coincidentally therewith producing an e.m.f. related thereto,
 said e.m.f.'s being designated $E_c$, $E_i$, and $E_h$, and being respectively produced in said cold, inlet, and hot streams,
 amplifying means for amplifying each said e.m.f.,
 a pair of low gain differential amplifying means for receiving each of said amplified e.m.f.'s; one said differential means receiving the amplified $E_c$ and $E_i$ signals, and another of said differential means receiving the amplified $E_h$ and $E_i$ signals,
 said one differential means producing an output signal, designated $E_i - E_c$, representing the difference between said two inputs thereto,
 said other differential means producing an output signal, designated $E_h - E_i$, representing the difference between said two inputs thereto,
 said $e_i - E_c$ output signal being at all times greater in voltage value than said $E_h - E_i$ signal,
 junction means for sending said $E_i - E_c$ signal along two different paths, designated a first path and a second path,
 a voltage multiplier circuit arranged in two halves; the first half of which is disposed in said first path and receives as input said $E_i - E_c$ signal, and also a positive voltage signal described hereinafter,
 said first half producing an output signal having a current value proportional to the square of the average of the sum of said $E_i - E_c$ and said positive voltage signals,
 said second half being disposed in said second path and receiving as input said $E_i - E_c$ signal and also a negative voltage signal hereinafter described,
 said second half producing an output signal having a current value proportional to the square of the average of the difference between said negative and said $E_i - E_c$ voltage signals,
 transmitting means for passing to voltage-producing means the output from said first half multiplier circuit, said output having a current value diminished by the current flowing to the second half multiplier circuit, said voltage-producing means comprising, operational amplifier means of high input resistance and a resistor of low resistance in parallel therewith, both operative in combination to produce a negative voltage signal that is the product of said $E_i - E_c$ and said positive voltage signals, means for forming an average positive voltage signal which is the difference between said $E_h - E_i$ and said product signals, high gain amplifying means for receiving said average positive voltage signal and delivering as output an amplified positive quotient signal defined as $E_h - E_i/E_i - E_c$, unity gain inverting amplifying means for receiving said quotient signal and inverting it to a negative polarity, connecting means for transmitting the negative quotient signal to the exit end of said second half multiplier circuit to provide said described negative voltage signal, connecting means for transmitting said positive quotient signal from said high gain amplifying means to said first half of multiplier circuit to provide said described positive voltage signal, and connecting means for transmitting said positive quotient signal from said high gain amplifying means to a voltmeter having means relating said positive quotient signal to the molecular weight of said inlet gas.

3. Apparatus for determining the molecular weight of a flowing gas stream comprising in combination a vortex tube having an inlet for said stream, a vortex generation chamber for receiving the stream and separating it into a cold fraction and a hot fraction, and an outlet for each said fraction through which it extis from the tube as a stream, temperature-sensing means disposable in each stream for sensing the temperature thereof and coincidentally therewith producing an e.m.f. related thereto, said e.m.f.'s being designated $E_c$, $E_i$, and $E_h$, and being respectively produced in said cold, inlet, and hot streams, low gain differential amplifying means for receiving each of said e.m.f.'s; one of said means receiving the $E_c$ and $E_i$ signals, and another of said means receiving the $E_h$ and $E_i$ signals, said one differential amplifying means producing an output signal, designated $E_i - E_c$, representing the difference between said two inputs thereo, said other differential amplifying means producing an output signal, designated $E_h - E_i$, representing the difference between said two inputs thereto, said $E_i - E_c$ signal being at all times greater in voltage than said $E_h - E_i$ signal, junction means for applying said $E_i - E_c$ signal along two different paths, designated a first path and a second path, means for establishing a current-voltage relationship in said first path according to which a change in voltage produces a changed current having a value proportional to the square of the average of the sum of the voltage signals through said path, said means comprising a first resistor through which said $E_i - E_c$ signal passes, a second resistor parallel to the first and of equal value for receiving a positive voltage signal hereinafter described, a first junction where said resistors form an average voltage signal from the sum of said $E_i - E_c$ and said positive signals, positively biased diode means, through which said average voltage signal passes, characterized by exhibiting a current-voltage relationship such that current passing through it is proportional to the square of the voltage, the output of said diode means having a current value proportional to the square of the average of the sum of said $E_i - E_c$ and said positive voltage signals, means for establishing a current-voltage relationship in said second path according to which a change in voltage produces a changed current having a value proportional to the square of the average of the difference between the voltage signals through said path, said means comprising a third resistor through which said $E_i - E_c$ signal passes, a fourth resistor parallel to the third and of equal value therewith and having an exit end capable of receiving a negative bias by a negative voltage signal hereinafter described, a second junction where said resistors form an average voltage signal from the difference between said $E_i - E_c$ and said negative voltage signals, negatively biased diode means characterized by exhibiting a current-voltage relationship such that current passing through it is proportional to the square of the voltage, the output of said diode means having a current value proportional to the square of the average of the difference between said negative and said $E_i - E_c$ voltage signals, transmitting means for passing to voltage-producing means the output from the positive diode means, said output having a current value diminished by the current flowing to the negative diode means, said voltage-producing means comprising operational amplifying means of high input resistance, a fifth resistor parallel to the latter and operative therewith to produce a negative voltage signal that is the product of the said $E_i - E_c$ and said positive voltage signals, a third junction for receiving said product voltage, means for forming an average positive voltage signal which is the difference between said $E_h - E_i$ and said product signals, said means comprising a sixth and a seventh resistors that are in parallel, the latter of which also functions as a variable resistor, a fourth junction for receiving said average positive voltage signal, high gain amplifying means for receiving said average positive voltage signal from the fourth junction, amplifying the same, and delivering it to a fifth junction as a positive quotient signal defined as $E_h - E_i/E_i - E_c$, unity gain inverting amplifying means for inverting said positive quotient signal from the fifth junction to a negative polarity, connecting means for transmitting the negative quotient signal to said exit end of said fourth resistor in order to impose said described negative bias thereon, connecting means for transmitting said positive quotient signal from said fifth junction to said second resistor to provide said described positive voltage signal, and connecting means for transmitting said positive quotient signal from the fifth junction to a voltmeter having means relating said positive quotient signal to the molecular weight of said inlet gas.

* * * * *